United States Patent [19]

Bock et al.

[11] Patent Number: 4,760,538
[45] Date of Patent: Jul. 26, 1988

[54] METHOD AND APPARATUS FOR DETERMINATION OF THE THAWING POINT OF JET FUELS

[75] Inventors: Patrice Bock, Le Havre; Philippe Dutot, Fongueusemare, both of France

[73] Assignee: Compagnie de Raffinage et Distribution-Total France, Paris, France

[21] Appl. No.: 828,836

[22] Filed: Feb. 12, 1986

[30] Foreign Application Priority Data

Feb. 12, 1985 [FR] France .................. 85 01944

[51] Int. Cl.⁴ .............. G01N 25/02; G06F 15/46
[52] U.S. Cl. ................................. 364/557; 73/64.1; 364/550; 374/24; 374/25
[58] Field of Search ............ 374/16, 17, 19, 20, 374/24, 25; 364/510, 550, 557; 340/870.17; 73/53, 64.1

[56] References Cited

U.S. PATENT DOCUMENTS

| | | | |
|---|---|---|---|
| 3,213,668 | 11/1965 | Thompson | 374/24 |
| 3,577,765 | 5/1971 | Bertoglio et al. | 374/24 |
| 3,667,280 | 6/1972 | Simpson | 374/25 |
| 3,695,093 | 10/1972 | Hummel et al. | 374/25 |
| 3,861,877 | 1/1975 | Matharani et al. | 73/64.1 |
| 4,024,753 | 5/1977 | Ouvrard | 374/24 |
| 4,137,753 | 2/1979 | Woodle | 73/53 |
| 4,383,770 | 5/1983 | Boschung et al. | 364/557 |
| 4,484,821 | 11/1984 | Willcock | 374/24 |
| 4,601,587 | 7/1986 | Mathiprakasam | 374/16 |
| 4,659,550 | 4/1987 | Schildknecht | 73/64.1 |

FOREIGN PATENT DOCUMENTS

57-24850 2/1982 Japan .
1438754 6/1976 United Kingdom .

Primary Examiner—Parshotam S. Lall
Assistant Examiner—Kevin J. Teska
Attorney, Agent, or Firm—A. Thomas S. Safford

[57] ABSTRACT

A method and apparatus for determining the thawing point of jet fuels by first cooling a sample of the fuel until crystals appear and then heating the sample until the crystals disappear, detecting the point at which the crystals appear both thermally and optically, detecting the point at which the crystals disappear both thermally and optically and correlating the resulting measurements to obtain an indication of the thawing point.

19 Claims, 5 Drawing Sheets

METHOD AND APPARATUS FOR DETERMINATION OF THE THAWING POINT OF JET FUELS

The jet fuels used in aviation must possess very precise low-temperature stability characteristics governed by international standards. Thus, the temperature at which crystals appear as the jet fuel cools, and especially the temperature at which the crystals disappear (thawing point) upon reheating, are important specifications. The standard allows a spread of not more than 3° C. between the temperatures at which crystals appear and disappear.

An apparatus for the determination of the thawing point is already known. The apparatus comprises a Dewar flask filled with a liquid coolant in which a tight test tube containing a predetermined amount of jet fuel is immersed, an agitator, and a thermometer. The appearance of the product is monitored visually as a function of the temperature. The onset of turbidity with decreasing temperature is held to signal the appearance of crystals, and that temperature is noted. The disappearance of the crystals results in a return to limpidity, and that temperature is also noted.

However, determination by an operator of the thawing point by this manual method takes too long. Moreover, the repeatability of this method is relatively high, being of the order of 0.7° C.

The present invention has as its object to overcome the drawbacks of the manual method described above and to this end relates to a method for the automatic determination of the thawing point of jet fuel which is characterized in that it consists in:

Subjecting a sample of the jet fuel to a thermal cycle during which the temperature is lowered to the temperature at which crystals appear and then again raised;

performing a thermal analysis of the jet fuel by measuring at regular intervals of time during said cycle the temperature assumed by the jet fuel;

performing simultaneously an optical analysis of the jet fuel by measuring at the same times the state of light transmission through said sample;

converting these measurements to signals of thermal detection and to signals of optical detection, respectively; and transmitting said signals to a central data-processing unit, such as a microprocessor, which computes from these signals the temperatures of appearance of crystals by thermal detection and by optical detection, and the temperatures of disappearance of crystals by these two types of detection.

The appearance of crystals modifies, by diffraction, the state of light transmission through the sample, and upon the disappearance of the crystals the original optical characteristics are restored.

The method in accordance with the invention thus utilizes a double-detection system for the temperature at which crystals disappear. The monitoring of the consistency of the results by means of the data-processing unit assures an accuracy that is at least equivalent if not superior to that of the visual detection in accordance with the prior technique.

Moreover, this double-detection method is more reliable than a single-detection method since in a purely thermal determination minor pollution of the jet fuel might escape detection and a purely optical determination might indicate an off-specification jet fuel as a result of a simple deposit of frost on the outer wall of the vessel containing the sample of jet fuel.

Finally, carrying out the method in accordance with the invention takes an operator not longer than some ten minutes whereas the manual method requires about one hour.

The measurements of the temperature and of the state of light transmission may be carried out every second, and the analysis of the sample may be pursued up to a limiting negative temperature, for example, −65° C., established on the basis of the lowest temperature which an aircraft is apt to encounter in flight. If no irregularity, the appearance or disappearance of crystals, is observed, the processing unit transmits a message to that effect.

The processing unit also verifies that the temperatures of appearance of crystals determined by the two types of detection do not differ from each other by more than a predetermined value, which, for example, may be equal to the repeatability of the manual method. Similar verification is made of the temperatures of disappearance of crystals. If that difference is found to be greater than said predetermined value, the processing unit transmits a message to the effect that the jet fuel is probably contaminated.

The processing unit further verifies that the mean of the temperatures of disappearance of crystals detected thermally and detected optically, and the mean of the temperatures of appearance of crystals detected by these two methods, do not differ from each other by more than a second predetermined value established by the standards, for example, 3° C. If this is not the case, the processing unit indicates that the measurement is not in conformity with the standard and transmits a message suggesting that the test be started all over again.

The present invention further relates to an apparatus for the determination of the thawing point of a jet fuel by the aforesaid method, said apparatus being characterized in that it comprises:

A test tube, made of a transparent material, containing a predetermined amount of jet fuel in which an agitator and a temperature probe are immersed;

a source of a heat-transfer fluid, for example, nitrogen gas, intended to reheat the test tube as soon as the temperature of appearance of crystals has been detected by the central unit;

a cooling jacket, also made of a transparent material, which surrounds said test tube and in which a circulation of a cooling fluid supplied by the low-temperature source is maintained by means of a pump;

an optical detector comprising a source transmitting a light beam, conducted by a first optical fiber, and a device receiving the luminous intensity transmitted, conducted by a second optical fiber, these two optical fibers being disposed in the axis of the test tube, the first one outside the test tube in the direction of its bottom and the second one inside the test tube just below the surface of the jet fuel; and a central data-processing unit, such as a microprocessor, intended to compute on the one hand the temperatures of appearance of crystals from the measurements supplied by the temperature probe and the measurements supplied by the optical detector, and, on the other hand, the temperatures of disappearance of the crystals from both types of measurements.

One end of the receiving optical fiber is located in the test tube below the surface of the jet fuel, preferably at the focal point of the lens formed by the bottom of the test tube and by the jet fuel.

Advantageously, the apparatus in accordance with the invention further comprises a clock permitting the acquisition of the temperature (to within one-hundredth of a degree Celsius) and of the state of light transmission (in relation to a given threshold) at regular intervals of time; a digital readout for the instantaneous temperature measured; and a printer for the formatting of the results.

The starting of the circulation of the cooling fluid through the cooling jacket as well as the injection of the heat-transfer fluid are controlled by the central data-processing unit.

The invention will now be explained in detail with reference to the accompanying drawings, wherein.

Figure 3:
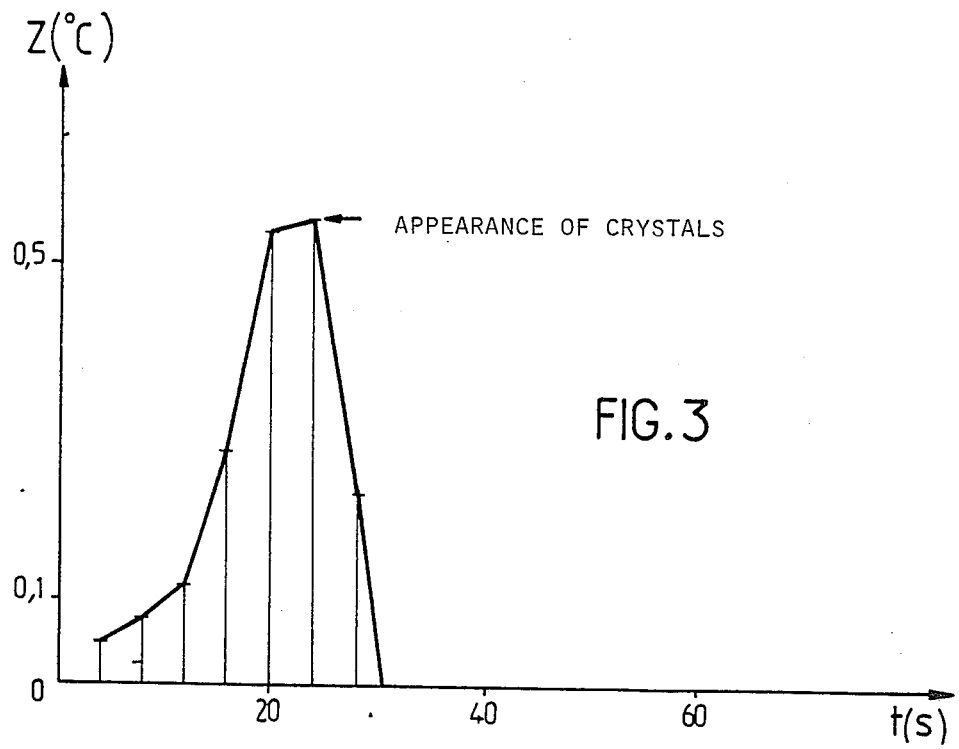
Figure 4:
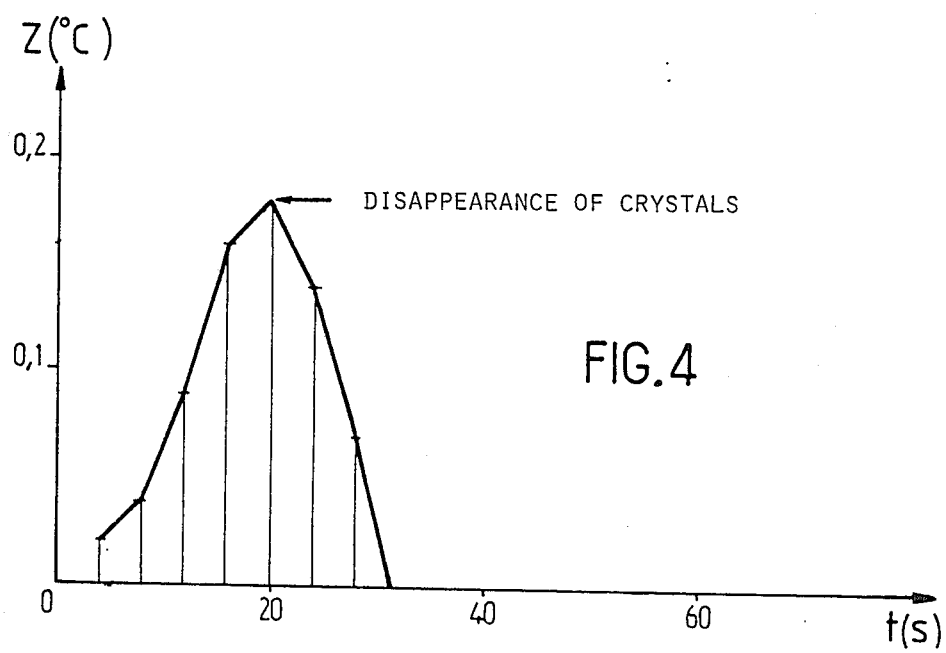
Figure 5A:
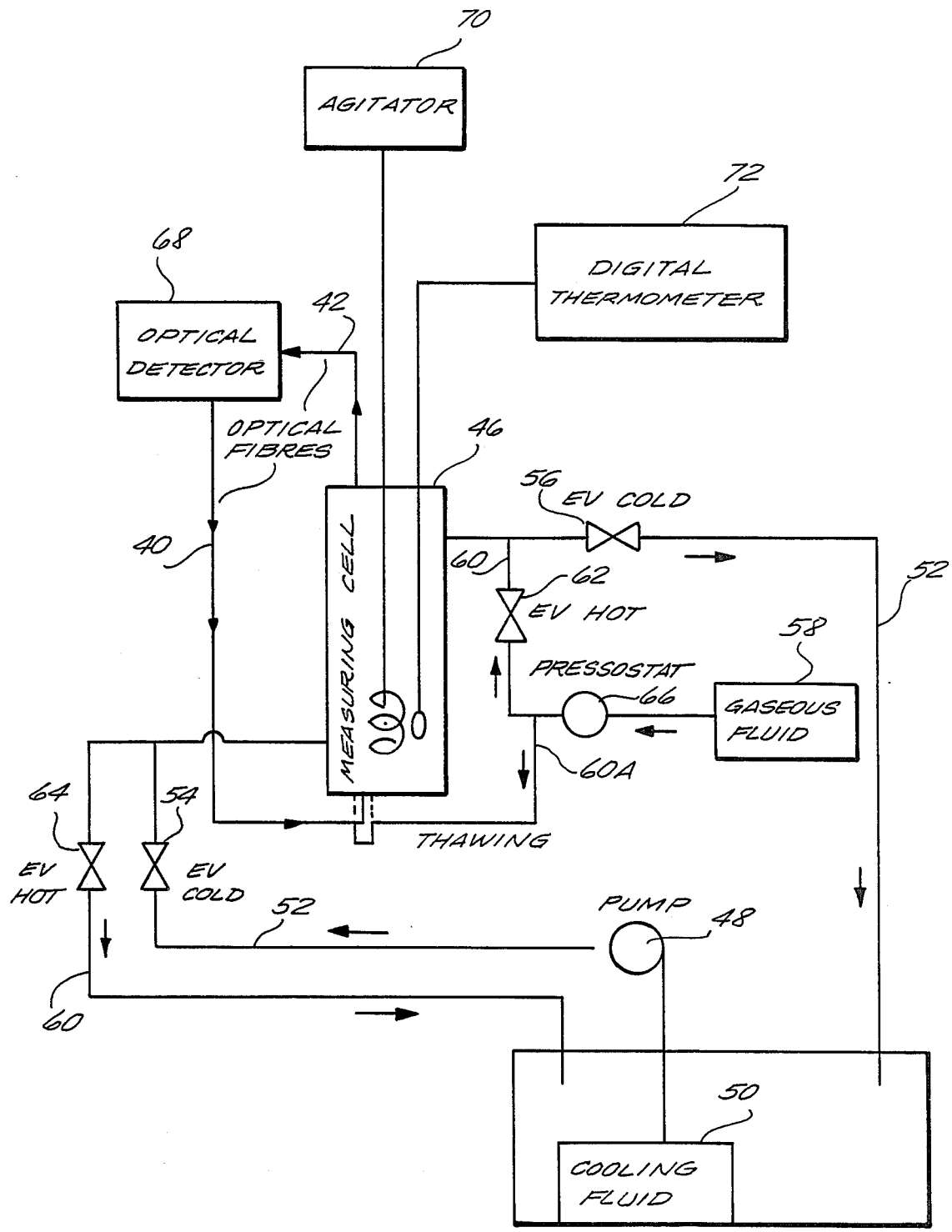
Figure 5B:
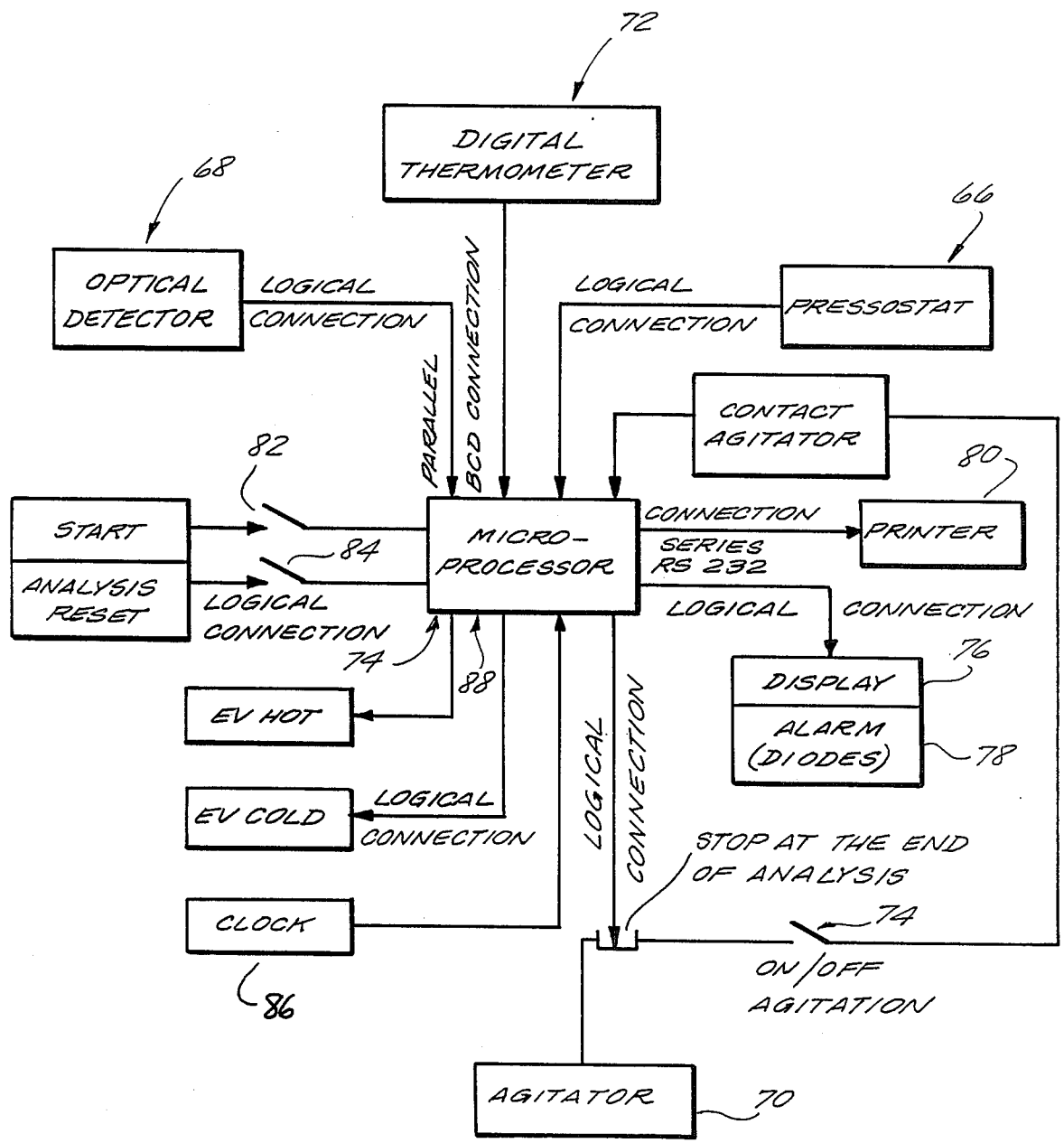

FIGS. 3 and 4 are representations of a function interpreting the variations of the second derivative in proximity to the point of appearance of crystals and in proximity to the point of disappearance of crystals, respectively; and FIGS. 5a and 5b are diagrammatic representations of the measuring, computing and auxiliary elements of the apparatus showing the relationship between these elements; wherein FIG. 5a shows the various constituents of the apparatus and the connection therebetween and FIG. 5b shows the information circuits (measurements and alarms).

Figure 1:
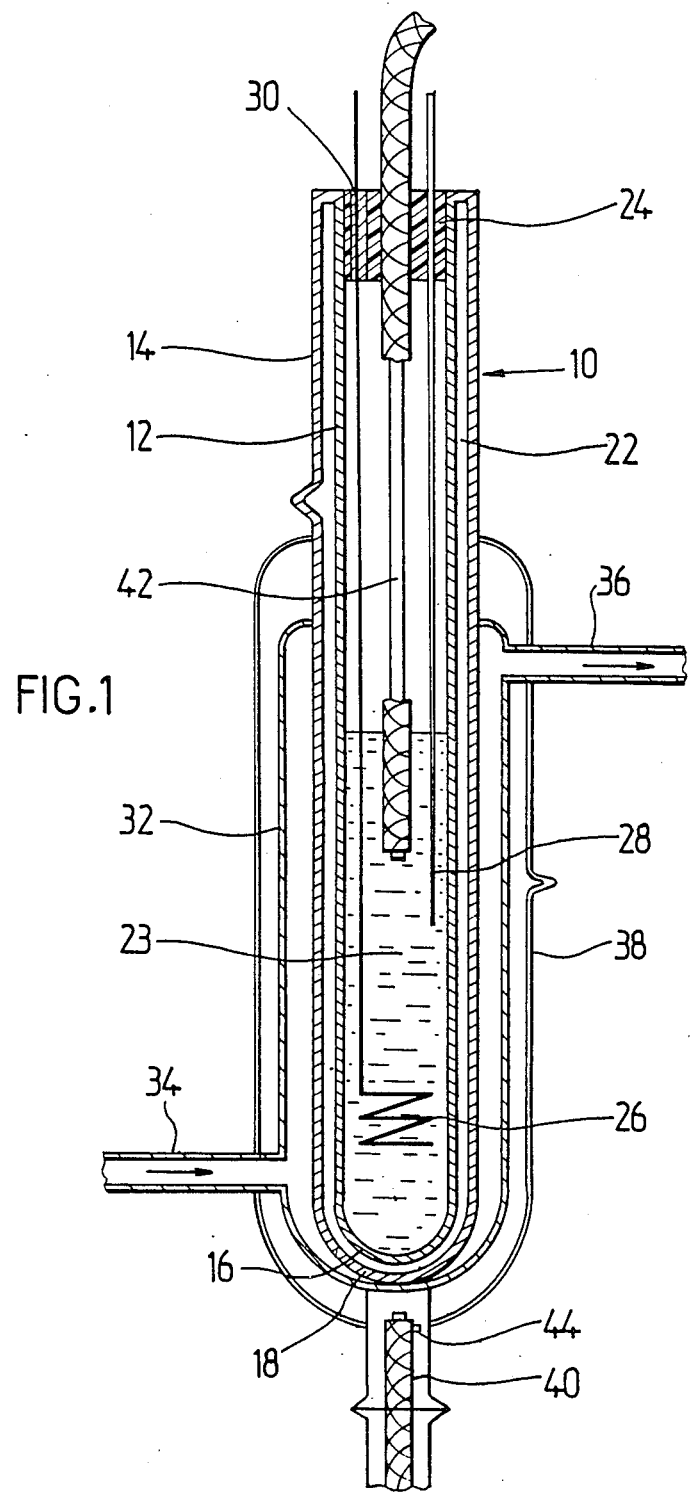
FIG. 1 is an axial sectional view of a measuring cell of the apparatus in accordance with a preferred embodiment the invention.

The apparatus for the automatic determination of the thawing point of a jet fuel comprises essentially a measuring cell, an exemplified embodiment of which is illustrated in FIGS. 1 and 5a.

This cell 46 comprises a double-jacket test tube 10 formed by two coaxial tubes 12, 14 having hemispherical bottoms 16, 18 and made of a transparent material. The space 22 between the two tubes is filled with dry air or dry nitrogen.

The test tube is filled with a predetermined volume of jet fuel 23 which under normal conditions of temperature and pressure is in liquid form. The test tube is disposed vertically and is hermetically sealed at its upper opening by a stopper 24.

An agitator element 26 and a temperature probe 28 are immersed in the jet fuel. The agitator is driven in an alternating vertical motion, preferably automatically, by motor means which are not shown. The agitator traverses the stopper within a sleeve 30 through which a light stream of dry nitrogen passes to protect the sample from any condensation of moisture.

The probe 28 traverses the stopper in a tight manner and is connected to a central data-processing unit, such as a microprocessor, which permits the automatic processing of the measurements and controls the execution of the process sequences.

The test tube 10 is surrounded by a cooling jacket 32, also made of a transparent material, provided with an inlet pipe connection 34 for a cooling fluid and with an outlet pipe connection 36 for said fluid, located in the lower part and in the upper part, respectively, of the jacket. The jacket 32 is connected in series with an immersed pump providing for the circulation of the cooling fluid at a constant flow rate.

Any cooling fluid may be used, for example, ethyl alcohol at −80° C. The operation of the pump is controlled by the microprocessor, as will be explained further on.

The cooling jacket 32 in turn is surrounded by a tight shell 38 under vacuum which provides heat insulation for the test tube.

The measuring cell further comprises a device for measuring the intensity of a light beam that has traversed the column of jet fuel contained in the test tube 10.

In the embodiment shown in FIG. 1, that device comprises a transmitting optical fiber 40, disposed axially outside the test tube 10 along its axis in such a way that one of its ends is a short distance from the bottom 18 of the test tube and that its other end is connected to a light source, not shown. The device further comprises a receiving optical fiber 42, mounted axially in the interior of the test tube in such a way that its lower end slightly dips below the surface of the jet fuel 23, preferably by the focal distance of the lens formed by the double bottom 16, 18 of the test tube and the jet fuel, and that its outer end is connected to a photosensitive element, not shown, such as a photoelectric cell intended to convert the incident luminous intensity into electrical signals which are processed by the microprocessor, as will be explained further on.

Advantageously, the photosensitive element is not subjected to the influence of ambient light in that a source of modulated light is used. It then is possible to work in ambient light.

The apparatus further requires a source of a gaseous fluid, for example, dry nitrogen, connected to a nozzle 44 which discharges below the bottom 18 of the test tube. A jet of dry nitrogen is injected continuously in such a way that no frost can form on the bottom 18, which might result in faulty optical measurements.

The reheating of the jet fuel at the conclusion of the cooling phase is effected by starting the circulation in the cell of a gas, for example, nitrogen, supplied by a source which is not shown. The admission of the nitrogen is likewise controlled by the microprocessor.

Referring now to FIG. 5a in conjunction with FIG. 1, an embodiment of the invention is shown schematically with the measuring cell 46 connected to various detection, control and other peripheral equipment as shown. The jacket 32 of the cell is connected in series with a circulating pump 48 providing for the circulation of a cooling fluid 50 at a constant flow rate. The cooling fluid is pumped into inlet pipe connection 34 through any suitable means well known in the art, such as, e.g., tubing. The cooling fluid then circulates throughout the jacket 32 and leaves the jacket via outlet pipe connection 36 and is carried via suitable means back to the supply 50 of cooling fluid. The pathway 52 along which the cooling fluid travels may be closed off by a pair of suitable valve means such as electrically controlled valves 54 and 56. The use of such valves in this situation is well known in the art.

Similarly, a gaseous fluid source 58 is connected to the cell 46. A pressurized gase, e.g., dry nitrogen is pumped along pathway 60 and introduced into the jacket 32 through outlet pipe connection 36. The gas circulates throughout the jacket 32 and exits the jacket through inlet pipe connection 34. The flow of gas along pathway 60 maybe stopped by a pair of valves such as electrically controlled valves 62 and 64. Again, the use of such valves in gas systems is well known in the art.

The gas is also connected by pathway 60A to nozzle 44 (see FIG. 1) which discharges below the bottom 18 of the test tube 10 (to prevent frost formation on the bottom 18 which might otherwise result in faulty optical measurements). Again, any suitable means for circulating the gas along pathway 60A maybe used such as, e.g., tubing. The rate of flow of the gas along pathways 60 and 60A is controlled by means well known in the art such as a pressostat 66.

Still referring to FIG. 5a in conjunction with FIG. 1, transmitting optical fiber 40 and receiving optical fiber 42 are connected to optical detector 68. Such an optical detector typically contains a light source (not shown) which is connected to one end of transmitting optical fiber 40 and a photosensitive element such as a photoelectric cell (not shown) which converts the incident luminous intensitve received by receiving optical fiber 42 into electrical signals which are then processed by a microprocessor. In addition, agitator 26 is shown connected to agitator motor 70. Further, probe 28 is connected to digital thermometer 72. The digital thermometer 72 provides a readout for the instantaneous temperature and also relays temperature data to a microprocessor.

Referring now to FIG. 5b, an embodiment of the apparatus in accordance with the invention may take the form of a cabinet (not shown) with a space reserved for the measuring cell. On the front panel of the cabinet may be mounted an on/off agitation switch 74, a display 76 indicating the state of advancement of the determination, an alarm module 78, a printer 80, a start button 82, a zero-reset button 84, an agitator 70, a clock 86 and a microprocessor 88. These panel components along with electrically controlled valves 54, 56, 62 and 64, pressostat 66, optical detector 68 agitator 70 and digital thermometer 72 are connected to microprocessor 88 via electrical connections and circuitry well known to one of ordinary skill in the art. These electrical connections and circuitry allow for the transmission of data to the microprocessor from the various data-collecting components such as the optical detector, digital thermometer and pressostat as well as electronic feedback control to the electrically controlled valves and electronic data output to the printer, display and alarm modules. Externally, the apparatus requires a supply of cooling fluid, a circulating pump for the cooling fluid and a nitrogen supply. The operation of the various components as set forth in FIGS. 5a and 5b are further illustrated in connection with the following description of the operation of the apparatus.

The apparatus in accordance with the invention operates in the following manner; An operator starts the apparatus by placing the switch into the ON position. Agitation begins and the circulating pump for the cooling fluid then starts and delivers to the cell a constant stream of fluid. The jet fuel then gradually cools at a typical rate of 1° C./minute, and its temperature as well as the state of light transmission are measured at regular intervals of time. Clock 86 enables the probe 28 and the optical-fiber detector 40, 42 to carry out the temperature measurements and the monitoring of the state of light transmission once per second, for example. These measurements are converted to signals which are routed to the microprocessor for processing.

When crystals appear in the jet fuel, they modify the state of light transmission by diffraction. At the same time, a plateau A appears on the descending leg of the temperature/time curve shown in FIG. 2. The microprocessor then records the temperature of appearance of crystals by optical detection, which will be designated AO, and computes by means of an algorithm that will be given further on the temperature of appearance of crystals by thermal detection, that is, AT.

Figure 2:
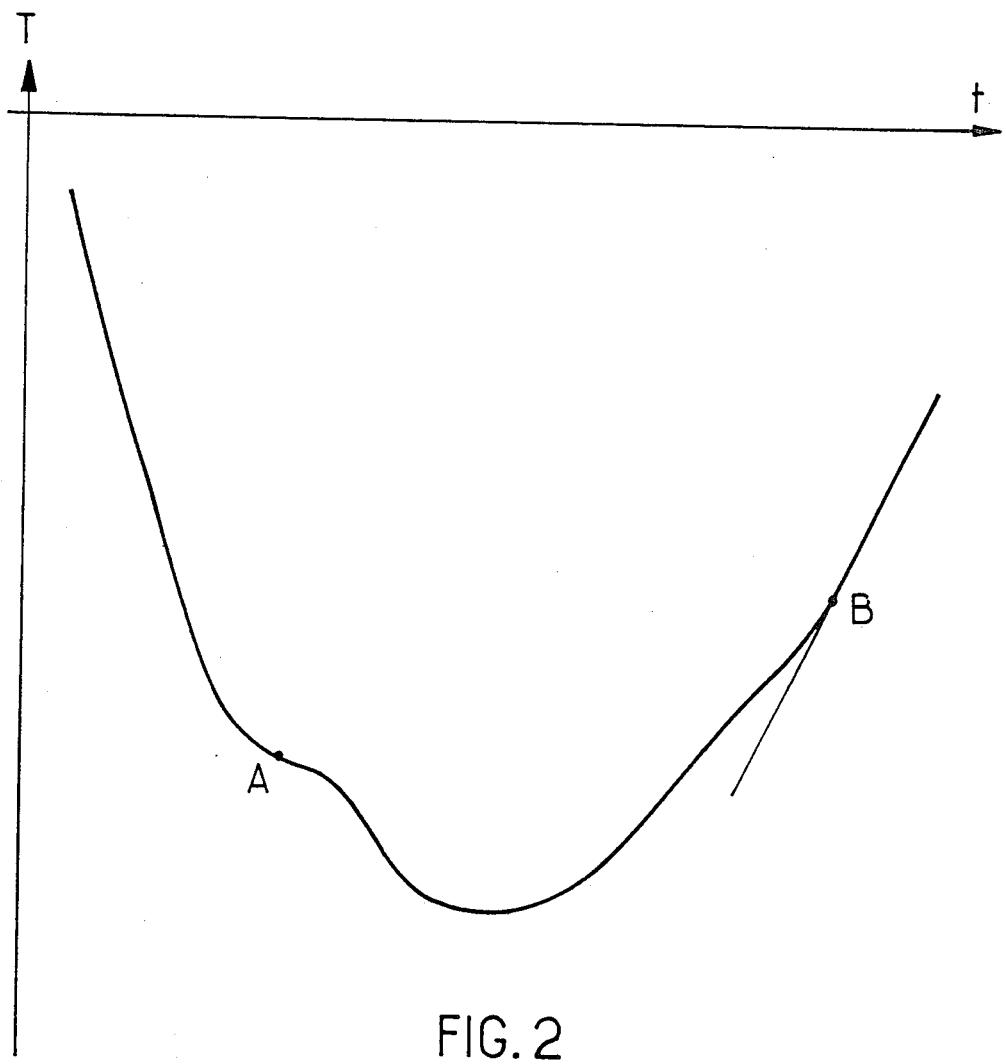
FIG. 2 is a typical thermoanalysis curve of a jet fuel.

Once these temperatures have been measured, the microprocessor causes the circulation of cooling fluid to stop and the circulation of nitrogen to start. The jet fuel then gradually heats up. The temperature and the state of light transmission are measured every second until the crystals have disappeared. That moment is reached when the light transmission is restored to its initial state. At that moment, point B on the ascending leg of the curve of FIG. 2 is reached where the slope attains a maximum before becoming constant. The microprocessor then acquires the temperature of disappearance of crystals by optical detection, that is, DO, and computes said temperature by thermal detection, that is, DT. It then carries out the following verifications:

$|AT-AO| < r$, r being the standardized repeatability of the manual method, which generally is assumed to be 0.7° C.

If this condition is not satisfied, contamination of the jet fuel is suspected and an appropriate message is printed and displayed.

A similar verification is carried out with respect to the quantity $|DT-DO|$. If that quantity is greater than r, contamination of the jet fuel is suspected.

Finally, with these two conditons satisfied, the microprocessor verifies further that $$\frac{DT + DO}{2} = \frac{AT + AO}{2} < 3° C.$$

If that condition is met, the message "Thawing point $$\frac{DT + DO"}{2}$$

is printed out, and if not, an appropriate message is displayed to prompt the resetting of the apparatus to zero and to start the analysis of the jet fuel all over again.

In the event that no irregularity is observed after the temperature has been lowered to −65° C., a message reading "Thawing point <60° C." is printed out.

In the very special case where the apparatus indicates a pseudoappearance of crystals based on thermal detection but without optical detection, a problem related to the rate of cooling (interruption of cooling-fluid feed) should be suspected. A message pointing out that irregularity is then printed out.

The algorithm used by the microprocessor for the determination of the points of appearance and disappearance of crystals on the basis of the thermal analysis will now be explained. The time t and the temperature T (to within one-hundredth of a degree Celsius) are recorded every second. With these records, the curve T =f(t) shown in FIG. 2 can be constructed. Since two successive records will, in practice, blend at the scale chosen for constructing this curve, the reasoning which follows will be based on records made at longer intervals of time, for example, every 20 seconds.

Thus, let t−20, t and t+20 be three successive instants spaced 20 seconds apart, and $T_{t-20}$, T and $T_{t+20}$ the corresponding temperatures.

Since the corresponding points on the curve 2 are relatively close-spaced, it may be assumed at first approximation that the quantities $$\frac{T_{t+20} - T_t}{20} \text{ and } \frac{T_t - T_{t-20}}{20}$$

are equal to the first derivative dT/dt of the function T=f(t) at the instants t and t−20, respectively.

Similarly, the quantity $$\frac{(T_{t+20} - T_t) - (T_t - T_{t-20})}{20 \times 20}$$

is substantially equal to the second derivative $d^2T/dt^2$ of said function at the instant t−20.

The beginning of the plateau A, created by the appearance of crystals, corresponds to a considerable variation of the cooling rate of the product, which manifests itself in an extremum of the second-derivative curve. The point B of disappearance of crystals corresponds to a maximum heating rate before the latter becomes nearly constant, which manifests itself in another extremum on the second-derivative curve.

Thus, to determine the points A and B, the microprocessor might try to find the extrema of the second derivative. However, such a determination is very imprecise since the function $d^2T/dt^2$ varies very little from zero.

With regard to the elimination of these difficulties, the following comments will be in order:

1. The microprocessor will determine the points sought, not on the basis of the second derivative but from the function $Z=(T_{t+20}-T_t)-(T_t-T_{t-20})$, which is proportional thereto. At each instant, the value assumed by that function is in fact 400 times greater than the value of the second derivative computed at the same instant. Since the variations of the function Z are more pronounced than those of the second derivative, it is obvious that the point sought can be determined more easily from that function.

2. FIGS. 3 and 4 show the values of |Z|, computed every second by the microprocessor and transferred every four seconds, in proximity to the point of appearance and to the point of disappearance, respectively, of crystals. For the disappearance of the crystals, the search for this maximum should be carried out over a sliding interval of 4° C.

As soon as the microprocessor has ascertained the extrema of |Z|, it proceeds with the verifications pointed out earlier of the corresponding values of the temperature by thermal detection and by optical detection, and if it finds that the values fully satisfy the conditions defined above (difference between these temperatures less than 3° C., and repeatability less than 0.7° C.), it causes them to be printed out.

An example of computation of the estimated repeatability is given below for a typical sample of jet fuel.

By the conventional manual method, the thawing point is found to be −53.5° C.

Ten measurements made by the method of the invention yielded the following values for the thawing point T:

| | |
|---|---|
| −53.03° C. | −52.90° C. |
| −53.93° C. | −52.87° C. |
| −52.98° C. | −52.82° C. |
| −52.93° C. | −52.98° C. |
| −52.98° C. | −52.84° C. |

The mean value of these measurements is $$T^* = \frac{\Sigma T_i}{n} = -52.96° \text{ C.}$$

and the standard deviation is $$s = \sqrt{\frac{\Sigma (T_i - T^*)^2}{n - 1}} = 0.068.$$

It is known that the estimated repeatability r is given by the formula $$r = t\sqrt{2}\ s;$$

where t is a random variable, known as a STUDENT factor (statistical table, calculated by the English chemist W. S. Gosset, who wrote under the name of STUDENT). If a 95% confidence limit is desired, the statistical tables give t=2.262.

Thus it is found that r=0.2° C.

The repeatability by the method of the invention thus is much lower than that of the manual method (0.7° C.). For the thawing point, a rounded value of −53° C. may be taken.

In conclusion, the method of the invention permits the thawing point to be defined with greater accuracy than the manual method. The determination by the method of the invention in fact takes an operator ten minutes at most, whereas the manual method requires about a full hour, with the operator having to be present throughout the measurement.

On the other hand, the double-detection method makes possible the elimination of the errors inherent in single-detection methods, whether thermal or optical.

We claim:

1. Method for an automatic determination of the thawing point of a jet fuel, comprising:
   subjecting a sample of the jet fuel to a thermal cycle during which the temperature is lowered to the temperature at which crystals appear and then raised until the crystals disappear, or the temperature is lowered to at least a predetermined value in the absence of crystals appearing prior thereto;
   performing a thermal analysis of the jet fuel by measuring relative to elapsed time during said cycle the temperature fluctuation of the jet fuel;
   performing simultaneously an optical analysis of the jet fuel by measuring the degree of light transmission through said sample with sufficient frequency of measurement over time to detect the time of change in transmission resulting from the appearance or disappearance of crystals;
   converting these measurements to signals of thermal detection and to signals of optical detection, respectively;
   transmitting said signals to a data-processing means; and
   using said means to compute from these signals the temperatures of appearance of crystals by thermal detection and by optical detection, respectively, and the temperatures of disappearance of crystals by these same two types of detection.

2. Method according to claim 1, wherein the thermal measurements are made at regular intervals of time.

3. Method according to claim 2, wherein in the absence of the appearance of crystals the cooling of the sample is pursued until the temperature has been lowered to $-65°$ C.

4. Method according to claim 2, wherein the processing means verifies that the temperatures of appearance of crystals determined by the two types of detection do not differ from each other by more than a first predetermined value that is equal to the repeatability of the method and said processing means makes a similar verification with respect to the temperatures of disappearance of crystals determined by the two types of detection.

5. Method according to claim 2, wherein the processing means verifies whether the mean of the temperatures of disappearance of crystals by thermal detection and by optical detection, and the mean of the temperatures of appearance of crystals by these two types of detection, do not differ by more than a predetermined value established by a given standard.

6. Method according to claim 5, wherein said predetermined value is on the order of $3°$ C.

7. Method according to claim 1, wherein the processing means determines the temperatures of appearance and of disappearance of crystals by thermal detection by:

recording at short intervals of time $\Delta t$, at least as often as about every second the temperature $T_t$ of the jet fuel as it is being cooled;

continuously computing the quantity $Z = (T_{t-\Delta t} - T_t) - (T_t - T_{t+\Delta t})$ representative of the variations of the second derivative of the temperature as a function of the time, $T_{t-\Delta t}$, $T_t$ and $T_{t+\Delta t}$ being the temperatures recorded at the instants $t-\Delta t$, t and $t+\Delta t$ spaced apart by a relatively short interval of time $\Delta t$;

and determining the temperatures for which Z reaches its extrema in the cooling phase and in the heating phase, respectively, these temperatures being the temperatures of appearance and disappearance, respectively, of crystals by thermal detection.

8. Method according to claim 2, wherein the processing means determines the temperatures of appearance and of disappearance of crystals by thermal detection by:

recording the temperature $T_t$ of the jet fuel every second as it is being cooled;

continuously computing the quantity $Z = (T_{t-\Delta t} - T_t) - (T_t - T_{t+\Delta t})$ representative of the variations of the second derivative of the temperature as a function of the time, $T_{t-\Delta t}$, $T_t$ and $T_{t+\Delta t}$ being the temperatures recorded at the instants $t-\Delta t$, t, and $t+\Delta t$ spaced apart by a relatively short interval of time $\Delta t$;

and determining the temperatures for which Z reaches its extrema in the cooling phase and in the heating phase, respectively, these temperatures being the temperatures of appearance and disappearance, respectively, of crystals by thermal detection.

9. Method according to claim 3, wherein the processing means determines the temperatures of appearance and of disappearance of crystals by thermal detection by:

recording the temperature $T_t$ of the jet fuel every second as it is being cooled;

continuously computing the quantity $Z = (T_{t-\Delta t} - T_t) - (T_t - T_{t+\Delta t})$ representative of the variations of the second derivative of the temperature as a function of the time, $T_{t-\Delta t}$, $T_t$ and $T_{t+\Delta t}$ being the temperatures recorded at the instants $t-\Delta t$, t, and $t+\Delta t$ spaced apart by a relatively short interval of time $\Delta t$;

and determining the temperatures for which Z reaches its extrema in the cooling phase and in the heating phase, respectively, these temperatures being the temperatures of appearance and disappearance, respectively, of crystals by thermal detection.

10. Method according to claim 4, wherein the processing means determines the temperatures of appearance and of disappearance of crystals by thermal detection by:

recording the temperature $T_t$ of the jet fuel every second as it is being cooled;

continuously computing the quantity $Z = (T_{t-\Delta t} - T_t) - (T_t - T_{t+\Delta t})$ representative of the variations of the second derivative of the temperature as a function of the time, $T_{t-\Delta t}$, $T_t$ and $T_{t+\Delta t}$ being the temperatures recorded at the instants $t-\Delta t$, t, and $t+\Delta t$ spaced apart by a relatively short interval of time $\Delta t$;

and determining the temperatures for which Z reaches its extrema in the cooling phase and in the heating phase, respectively, these temperatures being the temperatures of appearance and disappearance, respectively, of crystals by thermal detection.

11. Method according to claim 5, wherein the processing means determines the temperatures of appearance and of disappearance of crystals by thermal detection by:

recording every second the temperature $T_t$ of the jet fuel every second as it is being cooled;

continuously computing the quantity $Z = (T_{t-\Delta t} - T_t) - (T_t - T_{t+\Delta t})$ representative of the variations of the second derivative of the temperature as a function of the time, $T_{t-\Delta t}$, $T_t$ and $T_{t+\Delta t}$ being the temperatures recorded at the instants $t-\Delta t$, t, and $t+\Delta t$ spaced apart by a relatively short interval of time $\Delta t$;

and determining the temperatures for which Z reaches its extrema in the cooling phase and in the heating phase, respectively, these temperatures being the temperatures of appearance and disappearance, respectively, of crystals by thermal detection.

12. Apparatus for determination of the thawing point of a jet fuel comprising a test tube made of a transparent material for containing a predetermined amount of jet fuel, an agitator for said test tube, a temperature probe in said test tube for generating temperature measurements, a cooling jacket made of a transparent material which surrounds at least a significant portion of said test tube, a pump means for circulating cooling fluid through said cooling jacket, a source of a heat-transfer fluid for reheating the test tube, means for circulating said heat-transfer fluid after the temperature of appearance of crystals has been detected, an optical detector comprising a light beam transmitting source including a first optical fiber and a device for receiving and generating measurements of the intensity of the light transmitted thereto including a second optical fiber, said two optical fibers being disposed along the axis of the test tube, the first optical fiber being outside the test tube aligned in the direction of the tube's bottom, and the second optical fiber being inside the tube positionable just below the surface of any jet fuel contained therein; and a data-processing means for computing on the one hand the temperature of appearance of crystals from the measurements supplied by the temperature probe and the measurements supplied by the optical detector, and, on the other hand, the temperatures of disappearance of the crystals from both types of measurements.

13. Apparatus according to claim 12, wherein the second optical fiber is connected to a photosensitive element, the transmitting first optical fiber is mounted axially outside the test tube, in the direction of the bottom thereof, and the receiving second optical fiber is disposed axially inside the test tube in such a way that its receiving end is capable of being immersed below the surface of the predetermined amount of jet fuel, the curved bottom of said tube and said jet fuel sample forming a lens having a focal point within the body of fuel and the lower end of said second optical fiber being located at said focal point.

14. Apparatus according to claim 12, comprising a clock controlling the taking of temperature measurements and the detection of the degree of light transmission at regular time intervals by means of the temperature probe and the optical detector, respectively.

15. Apparatus according to claim 13, comprising a clock controlling the taking of temperature measurements and the detection of the degree of light transmission at regular time intervals by means of the temperature probe and the optical detector, respectively.

16. Apparatus according to claim 12, further comprising an on/off switch, a display controlled by said processing means indicating the state of advancement of the determination, an agitator module, an alarm module, a start button, a zero-restart button for the processing means, a printer and a digital readout for the instantaneous temperature, a panel for mounting the foregoing, a cabinet faced by said panel in which are incorporated the measuring cell and the processing means, a source of cooling fluid together with said circulating pump for said fluid, and said source of heat-transfer fluid being located outside said cabinet.

17. Apparatus according to claim 13, further comprising an on/off switch, a display controlled by said processing means indicating the state of advancement of the determination, an agitator module, an alarm module, a start button, a zero-restart button for the processing means, a printer and a digital readout for the instantaneous temperature, a panel for mounting the foregoing, a cabinet faced by said panel in which are incorporated the measuring cell and the processing means, a source of cooling fluid together with said circulating pump for said fluid, and said source of heat-transfer fluid being located outside said cabinet.

18. Apparatus according to claim 14, further comprising an on/off switch, a display controlled by said processing means indicating the state of advancement of the determination, an agitator module, an alarm module, a start button, a zero-restart button for the processing means, a printer and a digital readout for the instantaneous temperature, a panel for mounting the foregoing, a cabinet faced by said panel in which are incorporated the measuring cell and the processing means, a source of cooling fluid together with said circulating pump for said fluid, and said source of heat-transfer fluid being located outside said cabinet.

19. Apparatus according to claim 15, further comprising an on/off switch, a display controlled by said processing means indicating the state of advancement of the determination, an agitator module, an alarm module, a start button, a zero-restart button for the processing means, a printer and a digital readout for the instantaneous temperature, a panel for mounting the foregoing, a cabinet faced by said panel in which are incorporated the measuring cell and the processing means, a source of cooling fluid together with said circulating pump for said fluid, and said source of heat-transfer fluid being located outside said cabinet.

* * * * *